United States

Roule et al.

[11] 3,974,684
[45] Aug. 17, 1976

[54] ULTRASONIC SYSTEM FOR FOCUSING AT AN OBLIQUE ANGLE OF INCIDENCE

[75] Inventors: Maurice Roule, St-Georges; Robert Saglio, Massy, both of France

[73] Assignee: Commissariat a l'Energie Atomique, Paris, France

[22] Filed: Mar. 28, 1974

[21] Appl. No.: 455,858

[30] Foreign Application Priority Data
Apr. 2, 1973  France .................... 73.11736

[52] U.S. Cl. ................. 73/71.5 US; 73/67.8 R
[51] Int. Cl.² ........................................ G01N 29/04
[58] Field of Search ............. 73/67.5 R–67.9, 73/71.5 US

[56] References Cited
UNITED STATES PATENTS
3,699,805   10/1972   Bayre .................... 73/67.6

OTHER PUBLICATIONS
W. W. Bayre et al., Ultrasonic Detection of Inclusions in Steel, Materials Evaluation, Feb. 1970, pp. 25–31.

*Primary Examiner*—Richard C. Queisser
*Assistant Examiner*—John P. Beauchamp
*Attorney, Agent, or Firm*—Lane, Aitken, Dunner & Ziems

[57] ABSTRACT

In a focusing ultrasonic system for detecting flaws in a part and obtaining a single focal point in the ambient medium, the ratio of the distances between the points of impact of the different rays of the ultrasonic beam on the separation surface of the part to the two focal points of the beam along two orthogonal planes as considered in the ambient medium is equal to:

$$\left(\frac{\cos i_1}{\cos i_2}\right)^2$$

where $i_1$ is the angle of incidence of a ray and $i_2$ is its angle of refraction.

7 Claims, 8 Drawing Figures

ULTRASONIC SYSTEM FOR FOCUSING AT AN OBLIQUE ANGLE OF INCIDENCE

This invention relates to a focusing ultrasonic system for testing a material and in particular for obtaining a real focus at one point or a group of given points of said material.

Ultrasonic systems of this type are primarily employed for detecting flaws in a part (the word "system" should be understood to have the same meaning as the expression "optical system"). In point of fact, simple considerations of physics show that provision must be made for an ultrasonic transducer of substantial diameter in order to obtain good focusing in a homogeneous medium at a given frequency. As the ultrasonic test beam passes through the second medium (namely the material constituting the part to be tested), the laws of refraction apply and it is observed in this case that the focal point (fictitious point of covergence of the ultrasonic beam) is ill-defined since the outermost parts of the ultrasonic system give rise to waves having an angle of incidence at the surface of the dioptric element located between the two media which becomes too far removed from the Gaussian conditions (these are well-known in optics). In the case in which the mean incidence of the beam is normal to the dioptric element, this phenomenon may already be appreciable; it becomes very considerable, however, in the case of angles of incidence which correspond to transverse-wave testing. The abrupt use of a focused beam in a medium gives rise in this case to aberrations which bring to nought the desired focusing effect in the second medium. In actual practise, applications involving the use of beams of this type in the form of transverse waves are very important and extend, for example, to the majority of welding tests.

The above-mentioned phenomenon is illustrated in a vertical sectional plane in the diagram of FIG. 1. In a particular condition of operation of the ultrasonic system, the active surface of the ultrasonic transudcer which is limited to the points P and P'' is assimilated with a portion of circle placed in the medium $M_1$. The axis OX separates the media $M_1$ and $M_2$. The diagram shows a plot of the propagation of the ultrasonic wave corresponding to the points P and P'' as well as to the point P' which corresponds to the center of the transducer. After refraction at the points B, B' and B'' of the surface of the dioptric element which is constituted by the media $M_1$ and $M_2$ (axis OX), focusing takes place at the following points: A'' in the case of point P'', A' in the case of point B' and A in the case of point B. It is therefore seen that in actual fact, there is not a focal point but a very broad zone.

It is readily apparent that, when making use of a transducer of this type, the interpretation of results and in particular the localization of a defect is highly inaccurate.

In the description which now follows and in the appended claims, reference will be made in the case of an ultrasonic system to a focal point (for example the point A) of the ultrasonic beam emitted by the system. This is intended to simplify the language although it is known that, in the case of a focusing ultrasonic system placed in a given medium, there is not in acutal fact a focal point of the beam but a cylindrical zone which surrounds the theoretical focal point. This cylindrical zone is often referred-to as a spindle.

The precise aim of the present invention is to provide a focusing ultrasonic system which overcomes the disadvantage mentioned above and makes it possible to correct these aberrations and to obtain a single focal point in the medium in which defects are to be located.

The focusing ultrasonic system of the present invention is characterized by an active surface formed from a portion of a surface of revolution having an axis which is perpendicular to the surface separating the article to be tested from the ambient medium, wherein at every point on said active surface the ratio of the distance from the point of impact with the surface of separation of an ultrasonic wave generated at said active surface point to (1) the focal point of the ultrasonic waves generated along a first curve on said active surface formed by the intersection of said surface of revolution and a first plane defined by (a) said axis of revolution, and (b) said active surface point and said impact point, and (2) the focal point of the ultrasonic waves generated along a second curve on said active surface formed by the intersection of said surface of revolution and a second plane which is (a) orthogonal to said first plane, and (b) includes said active surface point and said impact point, is equal to:

$$\left( \frac{\cos i_1}{\cos i_2} \right)^2$$

where $i_1$ is the angle of incidence of a ray, $i_2$ is its angle of refraction and the focal points referred to in (1) and (2) are the points at which said ultrasonic waves would be focused if said part and said ambient medium were identical.

In accordance with a preferred characteristic feature, the active surface of the transducer which is equivalent to said ultrasonic system is a portion of toric surface in which the radii of curvature are defined by the relations:

$$F_1 = OA \cdot (V/t) + h$$

and $$F_2 = OA \cdot \frac{V}{t} \cdot \left( \frac{\cos i_1}{\cos i_2} \right)^2 + h$$

where $V$ represents the ratio of velocities of sound in the surface of the part to be tested and the point at of the angle of refraction of the ultrasonic beam in the second medium, $h$ represents the distance between the center of the active surface of the transducer and the surface of the part to be tested as measured along the incident ray and OA represents the distance between teh surface of the part to be tested and the point at which the ultrasonic beam is to be focused.

It is apparent from the formulae given above that we have the following relation:

$$\left( \frac{\cos i_1}{\cos i_2} \right)^2 = \frac{F_2 - h}{F_1 - h}$$

and this clearly shows that the second set of formulae which give $F_2$ and $F_1$ is only one particular case of the first formula. In fact, the lengths $F_2 - h$ and $F_1 - h$ represent the distances defined in the previous paragraph.

In a first embodiment, the system is constituted by a transducer in which the active surface is a portion of toric surface having radii of curvature which are defined by the relations:

$$F_1 = OA \cdot (V/t) + h$$

and $$F_2 = OA \cdot \frac{V}{t} \cdot \left(\frac{\cos i_1}{\cos i_2}\right)^2 + h$$

where $V$, $t$, $OA$ and $h$ have the same meanings as above.

In a second embodiment, the system is constituted by a focusing ultrasonic transducer in which the active surface is a portion of spherical surface and by an ultrasonic lens interposed between said transducer and the part to be tested, that face of said lens which is directed towards the part being cylindrical whilst the other face is plane.

In a third embodiment, the system is constituted by a focusing ultrasonic transducer in which the active surface is a portion of spherical surface and by a cylindrical ultrasonic mirror.

A better understanding of the invention will in any case be obtained from the following description in which a number of embodiments of the invention are given by way of non-limitative example and in which reference is made to the accompanying figures, wherein.

Figure 1:
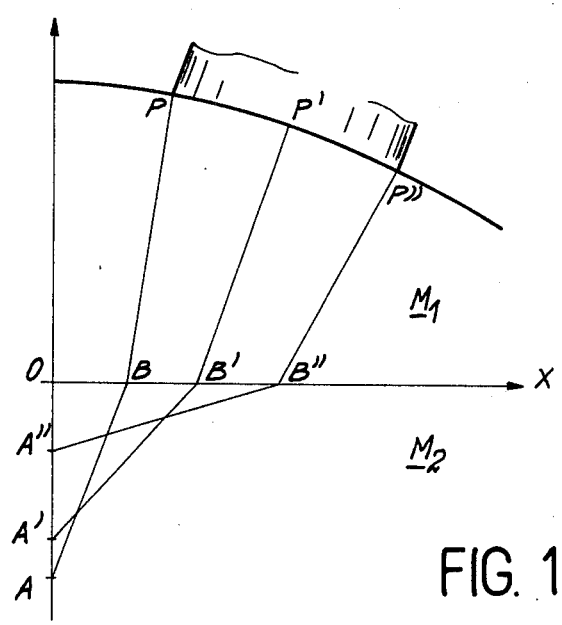
FIG. 1 shows the aberration effect produced by an ultrasonic beam of large diameter.
Figure 2:
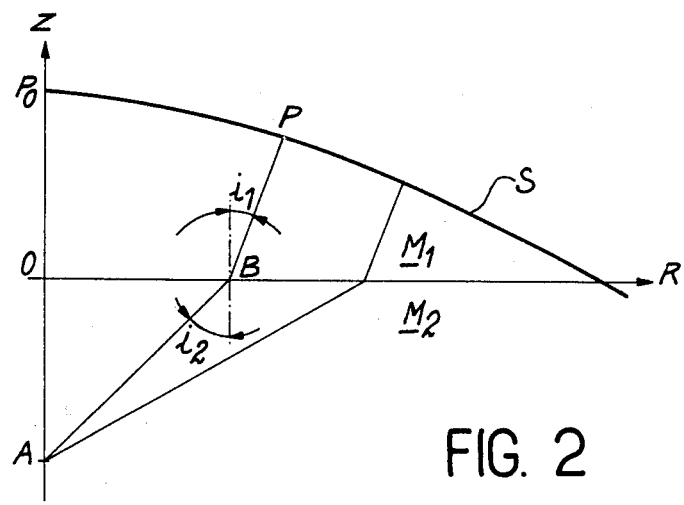
FIG. 2 shows the elements of determination of the equiphase surface.

The mode of determination of the equiphase surface is illustrated in FIG. 2, in which the media $M_1$ and $M_2$ are separated by a dioptric element represented by the straight line OR. It is desired to obtain a focus at the point A in the medium $M_2$. A beam issuing from the point P crosses the dioptric element at the point B, undergoes refraction and passes to the point A. The angle $i_1$ represents the angle of incidence of the beam and the angle $i_2$ represents the angle of refraction in the second medium. P is a point on the active surface of the transducer (equiphase surface) which is focused at the point A. The condition for ensuring that the point P forms part of such a surface lies in the relation:

$$\frac{AB}{V_2} + \frac{BP}{V_1} = T.$$

where $V_1$ represents the velocity of sound in the medium $M_1$, $V_2$ represents the velocity of sound in the medium $M_2$, $T$ represents the time of travel of the ultrasonic wave from the point P to the point A.

Moreover, it is known that the angles $i_1$ and $i_2$ are dependent on the relation;

$$\frac{\sin i_1}{V_1} = \frac{\sin i_2}{V_2}$$

in the case of $i_1 = 0$ (P at the point $P_o$) we have:

$$\frac{AO}{V_2} + \frac{OP_o}{V_1} = T$$

By equating the two expressions, we obtain:

$$\frac{AB}{V_2} + \frac{BP}{V_1} = \frac{AO}{V_2} + \frac{OP_o}{V_1}$$

The equiphase surface clearly has symmetry of revolution; the vertical axis of symmetry OZ passes through A and is perpendicular to the interface of the media $M_1$ and $M_2$. The equation of the surface therefore depends only on $r$ and on $z$ in cylindrical coordinates. By developing the calculations, it is found that the equations of the equiphase surface S relative to the point A is given by the relations:

$$r = \frac{1}{V} \sqrt{V^2 - 1 + t^2} \left[\frac{OA}{V \cdot t}(t-1) + OP_o\right]$$

$$z = \frac{1}{V} \sqrt{1 - t^2} \left[\frac{OA}{t}\left(V + \frac{t-1}{V}\right) + OP_o\right]$$

where each letter has the designation already given in the foregoing.

Figure 3:
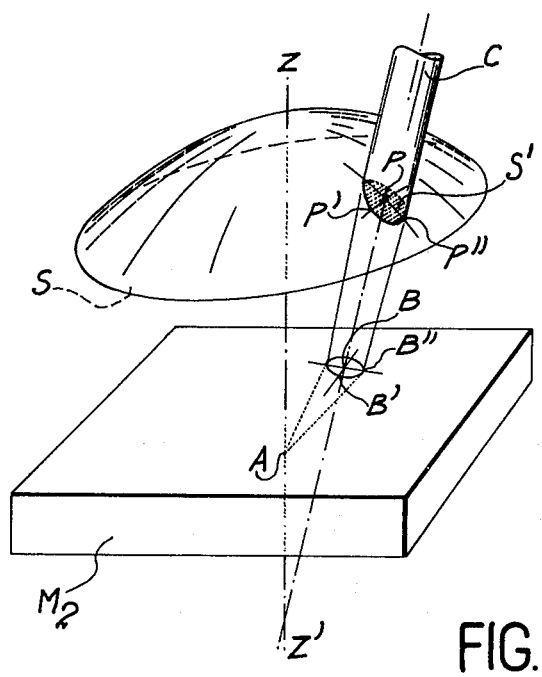
FIG. 3 is a perspective view of the equiphase surface.

FIG. 3 shows in perspective the equiphase surface S relative to the focus A within the medium $M_2$. The active surface of the transducer is the portion $S'$ of the surface S which is limited by the cylinder C and centered at the point P. There has been determined the radius of curvature of the surface $S'$ in the plane $ZZ'P$ and in a plane at right angles to said first plane and containing the straight line PB.

Researches undertaken by the inventor have shown that in the plane $BZZ'$, the radius of curvature is given by the relation:

$$F_2 = OA \cdot \frac{V}{t} \cdot \left(\frac{\cos i_1}{\cos i_2}\right)^2 + h$$

where $V$ represents the ratio of velocities of sound in the first and the second media, $t$ represents the cosine of the angle of refraction of the ultrasonic beam in the second medium, $OA$ represents the distance between the surface of the part to be tested and the point at which the ultrasonic beam is to be focused and $h$ represents the distance between the transducer and the dioptric element which separates the two media, and is equal to PB.

Similarly, the radius of curvature in the plane at right angles to the first plane is given by the formula: transducer $$F_1 = \frac{OA \cdot V}{t} + h$$

By giving the active surface of the ultrasonic transducer the shape of a toric surface in which the radii of curvature have been defined in the foregoing, there is obtained a very good approximation of the equiphase surface and machining of this latter is a much more simple operation.

In general, the researches carried out by the inventor have shown that, in order to correct the aberration, it is only necessary to ensure that the ratio of the distances of the points of impact of the different radii of the ultrasonic beam on the separation surface aforesaid to the two focal points of the beam along two orthogonal planes as considered in the ambient medium, as defined above, is equal to:

$$\left(\frac{\cos i_1}{\cos i_2}\right)^2$$

where $i_1$ is the angle of incidence of a ray and $i_2$ is its angle of refraction. This has been shown in FIG. 4. The dioptric element which separates the medium $M_1$ from the medium $M_2$ is represented schematically by the straight line x—x'. The straight line z—z' represents the direction of one ray of the ultrasonic beam emitted by the transducer 1. By reason of the difference between the media $M_1$ and $M_2$ (part to be tested), the ultrasonic ray follows the path HA in the medium $M_2$ and is focused at the point A. If the medium $M_2$ were identical with the medium $M_1$, all the ultrasonic rays of the beam would accordingly be focused at the point $F_2$ in the plane of the figure and at the point $F_1$ in the plane at right angles to the figure. The inventors have shown that, in order to have focusing at the point A, it is only necessary to ensure that the ratio of distance $HF_2$ to $HF_1$ in the case of each ray of the ultrasonic beam is equal to:

$$\left(\frac{\cos i_1}{\cos i_2}\right)^2$$

A focusing ultrasonic transducer is generally understood to mean a device which exists in two different forms:

1. a transducer in which the surface of the piezoelectric pellet is formed in such a manner as to result in focusing of the emitted ultrasonic beam;
2. a transducer in which the piezoelectric pellet is flat, a focusing lens being associated with said pellet and the surface of the lens being intended to cause focusing of the ultrasonic waves.

Figure 4A:
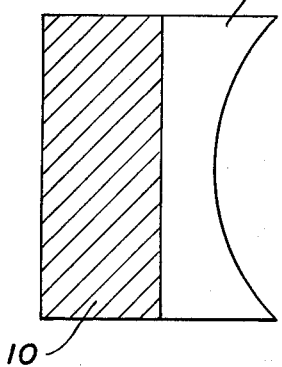
FIG. 4A is a view illustrating an embodiment in which the transducer contains a flat piezoelectric pellet with a focusing lens associated therewith.
Figure 4:
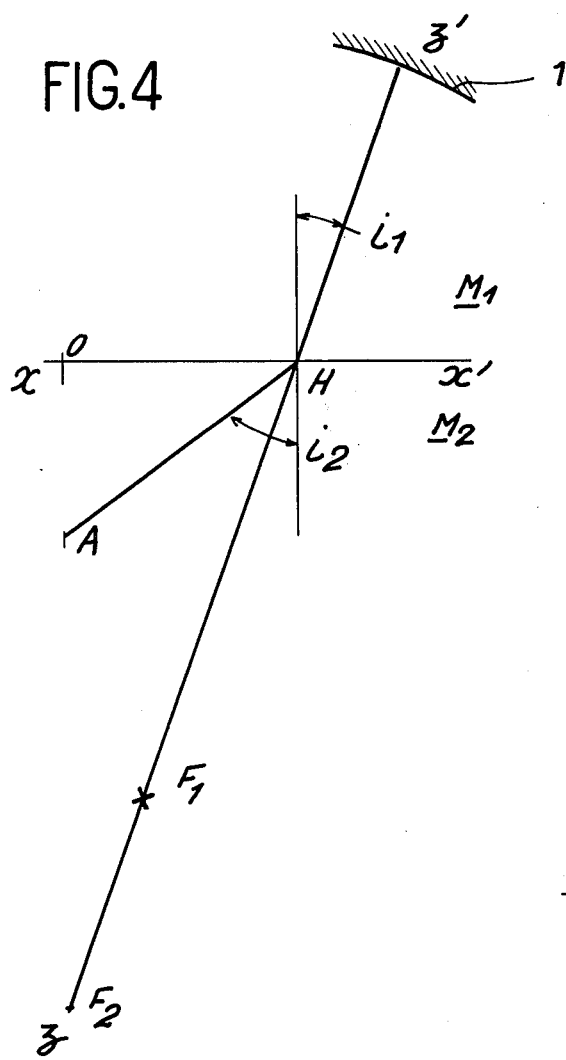
FIG. 4 is a view illustrating the determination of the ratio of focal distances in two orthogonal planes of the ultrasonic system.

This invention clearly applied to both types of transducer. In the case of the first type mentioned above, the active surface is the surface of the piezoelectric pellet which is in contact with the ambient medium ($M_1$). In the case of the second type, the radii of curvature of the focusing lens are calculated in known manner by means of the formulae:

$$R_1 = F_1 \times \frac{n-1}{n}$$

$$R_2 = F_2 \times \frac{n-1}{n}$$

where $n$ is the ratio of the velocities within the material which constitutes the lens and within the ambient medium ($M_1$). This embodiment is illustrated in FIG. 4A wherein the piezoelectric pellet is designated 10 and the focusing lens is designated 11.

Figure 5:
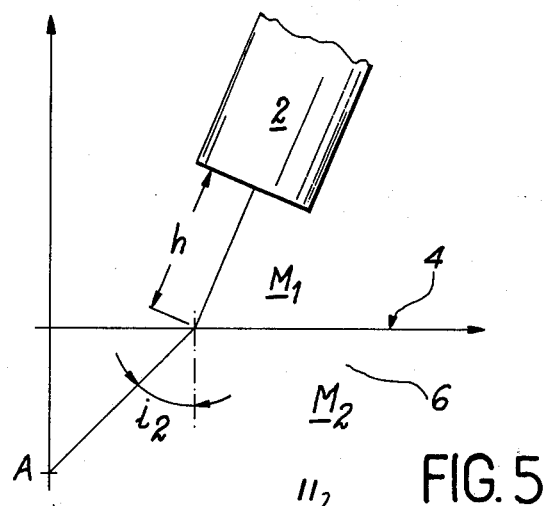
FIG. 5 shows one example of determination of the dimensions of a transducer.

FIG. 5 shows one example of determination of ultrasonic transducer in accordance with the invention for testing a part. The transducer 2 is placed in water (medium $M_1$) at a distance $h$ (86 mm in this example) from the surface 4 of the part 6 to be tested which is made of steel. The angle of refraction $i_2$ has a value of 45° and the point A at which focusing is to be obtained is located at 80 mm from the dioptric element which separates the two media.

A distance of 332 mm is accordingly obtained in the case of $F_1$ and a distance of 568 mm is obtained in the case of $F_2$. The focal spot has a diameter of 2.05 mm and a length in the steel of 20.84 mm.

It is readily apparent from the foregoing description that, in order to obtain focusing, it is necessary at the outset to make use of a transducer having a given active surface, to place the transducer at a given distance from the surface of the material to be tested and at a given angle of inclination. By displacing the transducer in a parallel direction, it is possible to scan the entire portion of the part which is located on each side of the depth equal to the distance OA and which is included in the focal zone. In order to scan the entire thickness of the part, it is necessary to make provision for additional transducers corresponding to different values of OA.

It can readily be understood that the portion S' of the surface S is not necessarily limited by a cylinder. In some applications, the surface S' can be limited by a prismatic surface (for example a surface having a rectangular transverse cross-section) in order to obtain a "spindle" having flat symmetry.

In the foregoing description, consideration has been given only to the case of a transducer alone. There would clearly not be any departure from the scope of the invention if the transducer alone were replaced by an ultrasonic system having the same characteristics. It would only be necessary to ensure in that case that the transducer which is equivalent to the complete ultrasonic system has the properties described in the foregoing.

Figure 6:
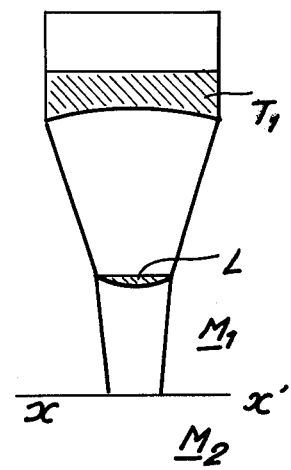
FIGS. 6 and 7 show alternative embodiments of the ultrasonic system in accordance with the invention.

There is shown in FIG. 6 a system constituted by a transducer $T_1$ having a spherical active surface associated with an ultrasonic lens L. It is only necessary to give the lens L a curvature such that the curvatures of the system in two orthogonal planes produce the ratio which was defined earlier.

Figure 7:
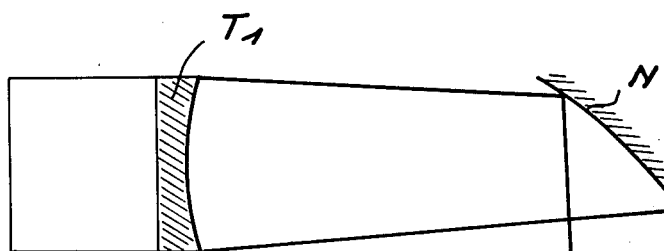

As in the example shown in FIG. 7, the cylindrical lens L could obviously be replaced by a cylindrical ultrasonic mirror N without of course having any effect on the final result.

The ultrasonic transducers have not been described in detail since anyone versed in the art is familiar with the design of transducers which make use of piezoelectric pellets and also with the electric circuits which are employed for producing the emission of the ultrasonic beam.

What we claim is:

1. A focusing ultrasonic system, which can be employed at any angle of incidence, for testing a part having a surface of separation from the ambient medium in which the ultrasonic system is placed and for producing a single focal point in said part, said system having an active surface formed from a portion of a surface of revolution having an axis which is perpendicular to said surface of separation and wherein at every point on said active surface the ratio of the distance from the point of impact with the surface of separation of an ultrasonic wave generated at said active surface point to
1. the focal point of the ultrasonic waves generated along a first curve on said active surface formed by the intersection of said surface of revolution and a first plane defined by
    a. said axis of revolution, and
    b. said active surface point and said impact point, and
2. the focal point of the ultrasonic waves generated along a second curve on said active surface formed by the intersection of said surface of revolution and a second plane which is
    a. orthogonal to said first plane, and
    b. includes said active surface point and said impact point, is equal to:

$$\left(\frac{\cos i_1}{\cos i_2}\right)^2$$

wherein $i_1$ is the angle of incidence of the ray, $i_2$ is its angle of refraction and the focal points referred to in (1) and (2) are the points at which said ultrasonic waves would be focused if said part and said ambient medium were identical.

2. A system according to claim 1, wherein the active surface is a portion of toric surface in which the radii of curvature are defined by the relations:

$$F_1 = OA \cdot V/t) + h$$

and $$F_2 = OA \cdot \frac{V}{t} \cdot \left(\frac{\cos i_1}{\cos i_2}\right)^2 + h$$

where $V$ represents the ratio of velocities of sound in the first and the second media, $t$ represents the cosine of the angle of refraction of the ultrasonic beam in the second medium, $OA$ represents the distance between the surface of the part to be tested and the point at which the ultrasonic beam is to be focused, and $h$ represents the distance between the center of the active surface and the surface of the part to be tested as measured along the incident ray.

3. A system according to claim 2, wherein said system is constituted by a transducer in which the active surface is a portion of toric surface having radii of curvature which are defined by the relations:

$$F_1 = OA \cdot (V/t + h$$

and $$F_2 = OA \cdot \frac{V}{t} \cdot \left(\frac{\cos i_1}{\cos i_2}\right)^2 + h$$

where $V$ represents the ratio of velocities of sound in the first and the second media, $t$ represents the cosine of the angle of refraction of the ultrasonic beam in the second medium, $OA$ represents the distance between the surface of the part to be tested and the point at which the ultrasonic beam is to be focused, and $h$ represents the distance between the center of the active surface of the transducer and the surface of the part to be tested as measured along the incident ray.

4. A system according to claim 3, wherein the active surface of said transducer is the surface of a pellet of piezoelectric material in contact with the ambient medium.

5. A system according to claim 3, wherein the active surface of said transducer is reconstituted by the associated of a flat pellet of piezoelectric material with a focusing lens such that the surface which is in contact with the ambient medium is a portion of toric surface having radii of curvature which are defined by the relations:

$$R_1 = F_1 \times \frac{n-1}{n}$$

$$R_2 = F_2 \times \frac{n-1}{n}$$

where $n$ represents the ratio of velocities within the medium which constitutes the lens and within the ambient medium.

6. A system according to claim 2, wherein said system is constituted by a focusing ultrasonic transducer in which the active surface is a portion of spherical surface and by a cylindrical ultrasonic lens interposed between said transducer and the part to be tested.

7. A system according to claim 2, wherein said system is constituted by a focusing ultrasonic transducer in which the active surface is a portion of spherical surface and by a cylindrical ultrasonic mirror.

* * * * *